(12) United States Patent
Itoh

(10) Patent No.: US 7,299,943 B2
(45) Date of Patent: Nov. 27, 2007

(54) AUTOMATIC DISPENSING TIP SUPPLY APPARATUS

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 347 days.

(21) Appl. No.: 10/724,710

(22) Filed: Dec. 2, 2003

(65) Prior Publication Data

US 2004/0108330 A1 Jun. 10, 2004

(30) Foreign Application Priority Data

Dec. 2, 2002 (JP) ............... 2002-350303

(51) Int. Cl.
*B65G 59/00* (2006.01)
*G07F 11/00* (2006.01)

(52) U.S. Cl. ............ 221/312 R; 221/242; 221/258

(58) Field of Classification Search ........ 221/265, 221/233, 236, 238, 239, 254, 263, 258, 312 R, 221/17, 192, 171, 164

See application file for complete search history.

(56) References Cited

U.S. PATENT DOCUMENTS

| | | | | |
|---|---|---|---|---|
| 488,084 A | * | 12/1892 | Miner | 221/238 |
| 3,228,553 A | * | 1/1966 | Breitenstein et al. | 221/6 |
| 3,777,932 A | * | 12/1973 | Matsui et al. | 221/204 |
| 4,567,997 A | * | 2/1986 | Portyansky | 221/233 |
| 4,860,922 A | * | 8/1989 | Malservisi et al. | 221/6 |
| 4,913,315 A | * | 4/1990 | Wagner | 221/200 |
| 4,948,012 A | * | 8/1990 | Snediker et al. | 221/195 |
| 4,991,748 A | * | 2/1991 | Hackmann et al. | 222/361 |
| 5,480,062 A | * | 1/1996 | Rogers et al. | 221/174 |
| 5,564,594 A | * | 10/1996 | Monfredo | 221/150 A |
| 5,568,881 A | * | 10/1996 | Chi | 221/175 |
| 5,704,516 A | * | 1/1998 | Yuyama | 221/164 |
| 6,039,209 A | * | 3/2000 | Yuyama et al. | 221/171 |
| 6,138,868 A | * | 10/2000 | Yuyama et al. | 221/312 R |
| 6,189,728 B1 | * | 2/2001 | Yuyama et al. | 221/17 |
| 6,199,720 B1 | * | 3/2001 | Rudick et al. | 221/6 |
| 6,505,756 B1 | * | 1/2003 | Walldorf et al. | 221/241 |

* cited by examiner

*Primary Examiner*—Gene O. Crawford
*Assistant Examiner*—Rakesh Kumar
(74) *Attorney, Agent, or Firm*—Nixon & Vanderhye P.C.

(57) ABSTRACT

An automatic dispensing tip supply apparatus includes a tip storing box whose bottom has a tapered surface having a tip collecting position in a lowermost part thereof to collect a plurality of inserted dispensing tips in one spot, a tip individually-sending mechanism which lifts up the collected dispensing tips one by one, an outlet to discharge the lifted dispensing tips from the tip storing box, a door mechanism including a door which is turnably supported to close the tip storing box from outside and a tip holding section which is provided on the inside of the door to horizontally hold one of the lifted dispensing tips, and a tip carry-out mechanism including a carry-out conveyor to automatically carry the dispensing tips.

2 Claims, 2 Drawing Sheets

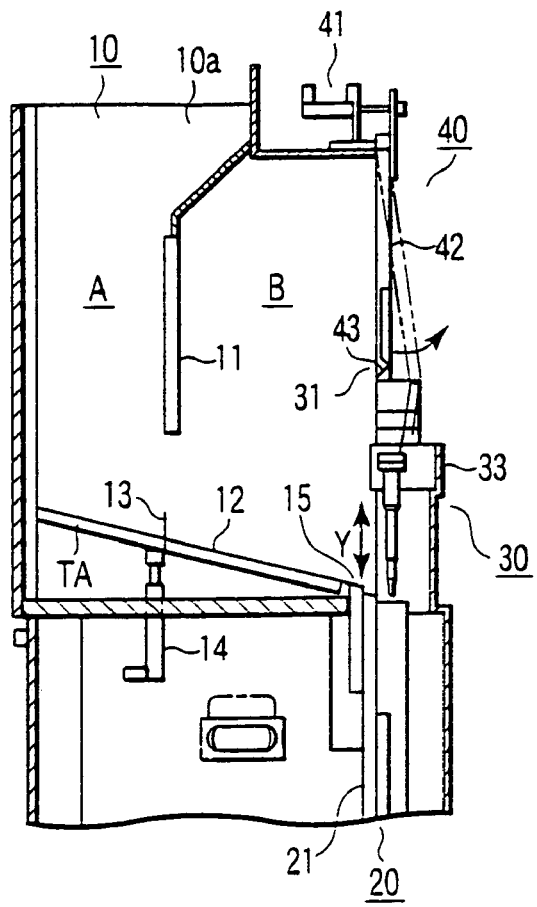
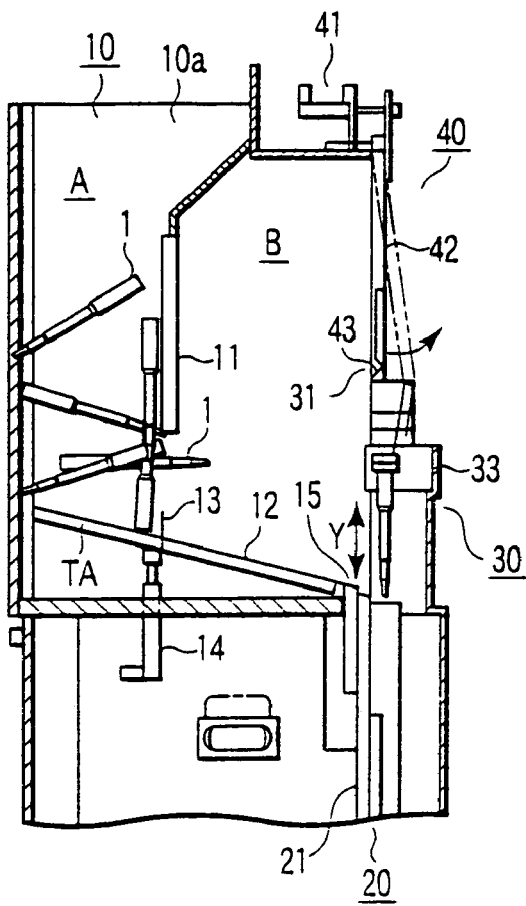
FIG. 1   FIG. 2
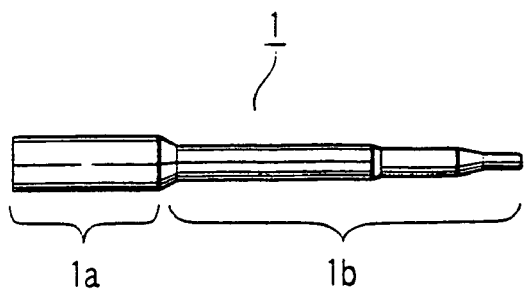
FIG. 3

AUTOMATIC DISPENSING TIP SUPPLY APPARATUS

CROSS-REFERENCE TO RELATED APPLICATIONS

This application is based upon and claims the benefit of priority from the prior Japanese Patent Application No. 2002-350303, filed Dec. 2, 2002, the entire contents of which are incorporated herein by reference.

BACKGROUND OF THE INVENTION

1. Field of the Invention

The present invention relates to an automatic dispensing tip supply apparatus for automatically supplying disposable dispensing tips that are used to dispense a large number of specimens such as blood and urine.

2. Description of the Related Art

In order to dispense a large number of specimens such as blood and urine, a large number of disposable dispensing tips are required. If a user purchases dispensing tips that are held in a rack, his or her running costs will increase. If a user purchases dispensing tips that are not held in a rack, he or she needs to expend much effort to hold the dispensing tips in a rack though they reduce in unit price. As conventional measures against this, an automatic supply apparatus using a parts feeder has been in practical use. However, this apparatus is so noisy that it makes work environment much worse. Furthermore, there is fear that the dispensing tips will be carried out overlapping each other.

BRIEF SUMMARY OF THE INVENTION

An object of the present invention is to provide an automatic dispensing tip supply apparatus having the following advantages.

1) The randomly inserted dispensing tips can be removed one by one and supplied to a position for use.

2) There is no fear that the dispensing tips will be carried out overlapping each other.

In order to attain the above object, an automatic dispensing tip supply apparatus according to the present invention has the following characteristic configuration. The other characteristic configurations will be clarified in the embodiment.

An automatic dispensing tip supply apparatus according to an aspect of the present invention, comprises a tip storing box whose bottom has a tapered surface having a tip collecting position in a lowermost part thereof to collect a plurality of dispensing tips in one spot through an insertion port; a tip individually-sending mechanism configured to lift up the dispensing tips, which are collected in the tip collecting position, one by one; an outlet formed to discharge the dispensing tips, which are lifted up by the tip individually-sending mechanism, from the tip storing box; a door mechanism including a door which is turnably supported at a top end thereof to close the tip storing box from outside and a tip holding section which is provided on an inside of the door to horizontally hold one of the dispensing tips lifted up by the tip individually-sending mechanism; and a tip carry-out mechanism including a carry-out conveyor to automatically carry the dispensing tips, which are dropped from the tip holding section when the door opens, out of the tip storing box through the outlet, wherein the tip holding section of the door mechanism includes a V-shaped groove which is formed in the door to insert a greater part $1b$ of one dispensing tip excluding at least a large-diameter proximal end portion and a tip stopping piece which is projected up toward a lower edge of the V-shaped groove.

BRIEF DESCRIPTION OF THE SEVERAL VIEWS OF THE DRAWING

FIG. 1 is a schematic sectional view of an automatic dispensing tip supply apparatus according to an embodiment of the present invention, in which no dispensing tips have been inserted.

FIG. 2 is a schematic sectional view of an automatic dispensing tip supply apparatus according to the embodiment of the present invention, in which dispensing tips have been inserted.

FIG. 3 is a side view showing an example of a dispensing tip supplied by the automatic dispensing tip supply apparatus according to the embodiment of the present invention.

DETAILED DESCRIPTION OF THE INVENTION (Embodiment)

Figures 4, 5A, 5B, 5C:
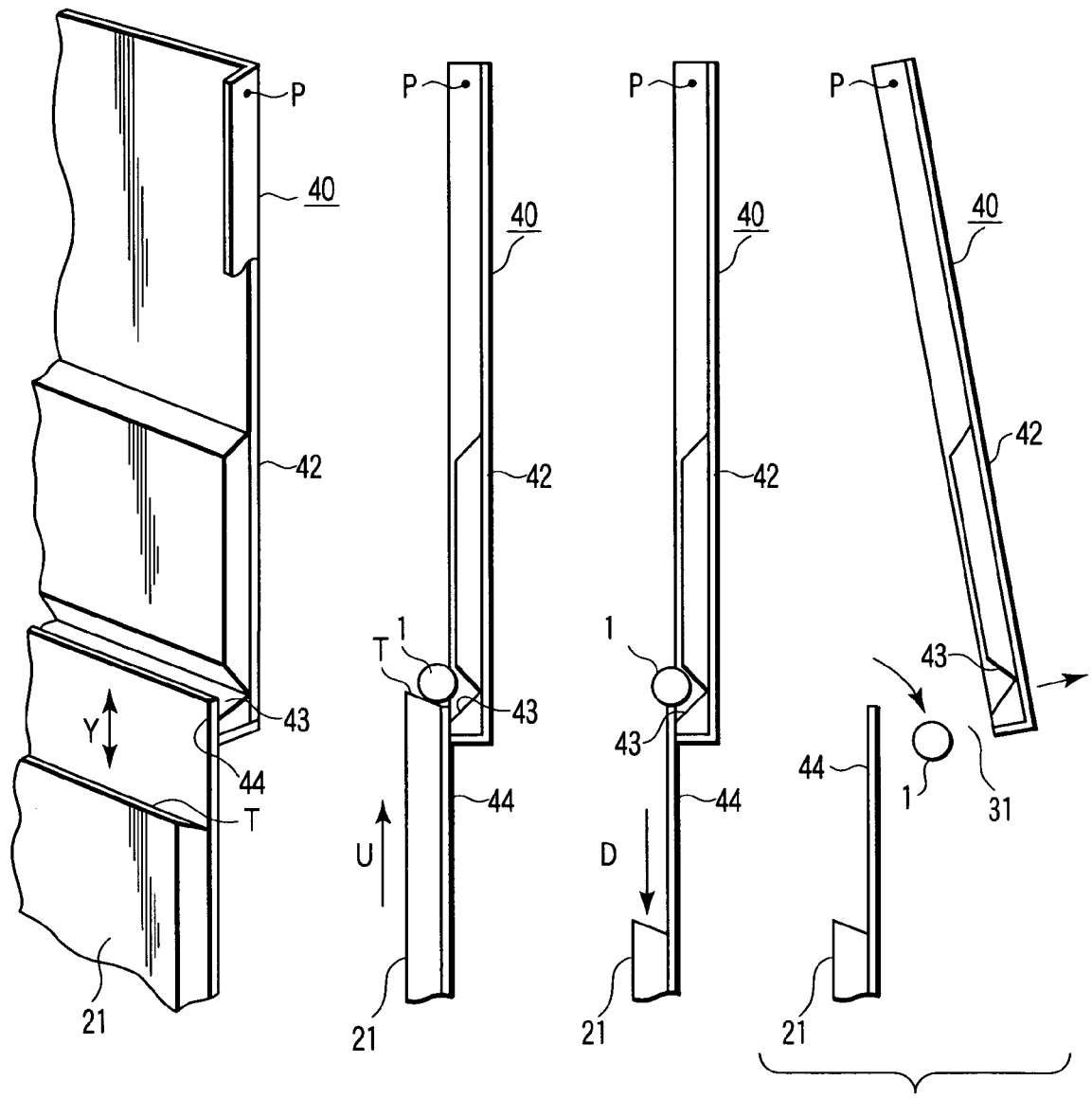
FIG. 4 is a perspective view of a main part of the automatic dispensing tip supply apparatus according to the embodiment of the present invention, which shows a relationship between a tip individually-sending mechanism and a door mechanism.
FIGS. 5A to 5C are illustrations of a tip discharging operation performed by the tip individually-sending mechanism.

FIGS. 1 and 2 illustrate a tip storing box 10 that is partitioned into rooms A and B by a partition plate 11. The room A has an insertion port 10a at its top end. The bottom 12 of the tip storing box 10 has a tapered surface TA. The tapered surface TA descends from one side to the other such that a plurality of resin or paper-made dispensing tips 1, which are randomly inserted through the insertion port 10a, can be collected in one spot. The box 10 has a stopper 13 at its bottom 12 to appropriately limit the number of dispensing tips 1 that slide on the tapered surface TA of the bottom 12. The stopper 13 can be projected up from the tapered surface TA by a drive source 14 such as an air piston cylinder device. A tip collecting position 15 is located in the lowermost part of the tapered surface TA.

A tip individually-sending mechanism 20 can lift up the dispensing tips 1, which are collected in the tip collecting position 15, one by one along one sidewall (not shown) of the box 10 located close to the tip collecting position 15.

The tip individually-sending mechanism 20 has a lifting plate 21 that is driven up and down as indicated by arrow Y by a drive source (not shown). The top end face of the lifting plate 21 has a space enough to place only one dispensing tip 1 lying on its side. The top end face is a tapered surface TB (see FIG. 4) that descends toward the outside of the tip storing box 10.

A tip outlet 31 is formed on the uppermost part of the one sidewall of the box 10 described above. The tip outlet 31 discharges the dispensing tips 1, which are lifted up by the tip individually-sending mechanism 20, from the tip storing box 10.

A door mechanism 40 closes the tip outlet 31 from outside the tip storing box 10. The door mechanism 40 is formed chiefly of a door 42. The door 42 is turnably supported at a point P (see FIG. 4) close to the top end thereof. The door 42 is opened and closed by a drive source 41 such as an air piston cylinder device. The door 42 has a tip holding section (43, 44) on its inner side. The tip holding section (43, 44) is formed as follows to horizontally hold one dispensing tip lifted up by the tip individually-sending mechanism 20.

As illustrated in FIG. 4, the tip holding section (43, 44) includes a V-shaped groove 43 and a tip stopping piece 44. The V-shaped groove 43 is formed in the door 42 to insert a greater part 1b of one dispensing tip excluding at least a large-diameter proximal end portion 1a. The tip stopping piece 44 projects up toward the lower edge of the V-shaped groove 43.

Returning back to FIG. 1, a tip carry-out mechanism 30 is provided outside the one sidewall of the tip storing box 10. This mechanism 30 includes a carry-out conveyor 33 for automatically carrying the dispensing tips 1, which are dropped from the tip holding section (43, 44) when the door 42 opens, out of the box 10 through the outlet 31.

An operation of the automatic dispensing tip supply apparatus having the above configuration will now be described. The dispensing tips 1 to be supplied automatically are randomly inserted into the room A through the insertion port 10a by hand. When the stopper 13 retracts for a short period of time, some of the inserted dispensing tips 1 slide from the room A to the room B and are collected in the tip collecting position 15 that is the lowermost part of the tapered surface TA. Of the dispensing tips 1 collected in the tip collecting position 15, the dispensing tips placed on the tapered surface TB of the top end face of the lifting plate 21 of the tip individually-sending mechanism 20 are lifted up to the level of the outlet 31 one by one as the lifting plate 21 rises.

If there are two or more dispensing tips 1 lifted up overlapping each other by the mechanism 20, the large-diameter proximal end portion 1a of each dispensing tip 1 will project from the V-shaped groove 43 of the tip holding section (43, 44). The center of gravity of each dispensing tip 1 therefore inclines toward the inside of the box 10. Consequently, the dispensing tip 1 drops again toward the bottom of the box 10 when the lifting plate 21 descends even though the distal end of the tip 1 is inserted into the V-shaped groove 43.

If there is one or more dispensing tips 1 lifted up in an upright position by the mechanism 20, they do not enter the V-shaped groove 43. The center of gravity of each dispensing tip 1 also therefore inclines toward the inside of the box 10. Consequently, the dispensing tip 1 drops again toward the bottom of the box 10 when the lifting plate 21 descends.

As a result, as shown in FIG. 5A, only one dispensing tip 1 is lifted up lying on its side by the lifting plate 21 as indicated by arrow U and its greater part 1b, excluding the large-diameter proximal end portion 1a, is inserted into the V-shaped groove 43 of the tip holding section (43, 44) provided in parallel to the door 42. The center of gravity of the dispensing tip 1 is narrowly maintained in the tip holding section (43, 44). The dispensing tip 1 continues to be held by the tip holding section (43, 44) even though the lifting plate 21 descends as indicated by arrow D in FIG. 5B.

When the door mechanism 40 operates and the door 42 opens as shown in FIG. 5C, the dispensing tips 1 held by the tip holding section (43, 44) are discharged from the outlet 31. The discharged dispensing tips 1 are automatically carried one by one out of the box 10 through the carry-out conveyor 33 and supplied to a given position for use. The above operation is performed each time the lifting plate 21 moves up and down.

(Features of the Embodiment)

[1] An automatic dispensing tip supply apparatus according to an embodiment, comprises:

a tip storing box 10 whose bottom 12 has a tapered surface TA having a tip collecting position 15 in a lowermost part thereof to collect a plurality of dispensing tips 1 in one spot through an insertion port;

a tip individually-sending mechanism 20 configured to lift up the dispensing tips 1, which are collected in the tip collecting position 15, one by one;

an outlet 31 formed to discharge the dispensing tips 1, which are lifted up by the tip individually-sending mechanism 20, from the tip storing box 10;

a door mechanism 40 including a door 42 which is turnably supported at a top end P thereof to close the tip storing box 10 from outside and a tip holding section (43, 44) which is provided on an inside of the door 42 to horizontally hold one of the dispensing tips lifted up by the tip individually-sending mechanism 20; and a tip carry-out mechanism 30 including a carry-out conveyor 33 to automatically carry the dispensing tips 1, which are dropped from the tip holding section (43, 44) when the door 42 opens, out of the tip storing box 10 through the outlet 31, wherein the tip holding section (43, 44) of the door mechanism 40 includes a V-shaped groove 43 which is formed in the door 42 to insert a greater part 1b of one dispensing tip excluding at least a large-diameter proximal end portion 1a and a tip stopping piece 44 which is projected up toward a lower edge of the V-shaped groove 43.

In the automatic dispensing tip supply apparatus described above, whenever the lifting plate 21 ascends, the dispensing tips 1 are lifted up to the outlet 31 and only the dispensing tips held by the tip holding section 943, 44) are discharged from the box. The randomly inserted dispensing tips 1 can thus be removed one by one and supplied to a position for use. Since, moreover, the dispensing tips 1 are selected by both restrictions on the space of the top end face of the lifting plate 21 and by the tip holding section (43, 44), there is no fear that the tips 1 will be carried out overlapping each other.

[2] In the automatic dispensing tip supply apparatus according to above item [1], the tip individually-sending mechanism 20 includes a lifting plate 21 which is driven up and down by a drive source, and the lifting plate 21 has a top end face having a space enough to place only one dispensing tip 1 lying on its side and a tapered surface TB that descends toward the outside of the tip storing box 10.

In the automatic dispensing tip supply apparatus described above, whenever the lifting plate 21 moves up, only one dispensing tip 1 lying on its side on the top end face of the plate 21 is lifted up to the tip holding section (43, 44) and supplied thereto. Thus, the possibility that one dispensing tip 1 is held by the tip holding section (43, 44) will be increased.

[3] In the automatic dispensing tip supply apparatus according to one of above items [1] and [2], the tip storing box 10 includes a stopper 13 on the tapered surface TA of the bottom 12, and the stopper appropriately limits the number of dispensing tips 1 that slide on the tapered surface TA.

In the automatic dispensing tip supply apparatus, the inserted dispensing tips 1 are supplied to the tip collecting position 15 with their number and position restricted. The dispensing tips 1 can be prevented from being collected to excess at once in the tip collecting position 15. Therefore, the lifting plate 21 can smoothly be moved up and down.

What is claimed is:

1. An automatic dispensing tip supply apparatus comprising:
   a tip storing box whose bottom is slanted and has a tip collecting section in a lowermost part thereof to collect a plurality of dispensing tips, each of the tips having a large-diameter section and a small-diameter section, the small-diameter section capable of being inserted into an opening of the large-diameter section, a length of the small-diameter section being larger than a length of the large-diameter section, and the tip storing box including an outlet positioned higher than the tip collecting section;
   a tip individually-sending mechanism configured to lift up the dispensing tips from the tip collecting section to the outlet;
   a door mechanism including a door which is turnably supported at a top end thereof to close the outlet of the tip storing box from outside and a tip holding section which is provided on an inside of the door to horizontally hold the small-diameter section of one of the dispensing tips lifted up to the outlet by the tip individually-sending mechanism; and
   a tip carry-out mechanism including a carry-out conveyor to carry the dispensing tips, which are dropped from the tip holding section when the door opens, out of the tip storing box through the outlet,
   wherein the tip holding section of the door mechanism includes a V-shaped groove which is formed in the door to have a size to hold the small-diameter section of one of the dispensing tips and a tip stopping piece to hold one of the tips lifted up to the outlet by the tip individually-sending mechanism within the V-shaped groove when the door closes, and
   wherein the tip individually-sending mechanism includes a lifting plate which is driven up and down by a drive source, and the lifting plate has a top end face having a space enough to place only one dispensing tip and a tapered surface that descends toward an outside of the tip storing box.

2. The automatic dispensing tip supply apparatus according to claim 1, wherein the tip storing box includes a stopper on the bottom, and the stopper appropriately limits the number of dispensing tips that slide on the bottom.

* * * * *